US00PP27815P3

(12) United States Plant Patent
Shock et al.

(10) Patent No.: US PP27,815 P3
(45) Date of Patent: Mar. 28, 2017

(54) ***STEVIA* PLANT NAMED 'SW 201'**

(50) Latin Name: *Stevia rebaudiana*
Varietal Denomination: SW 201

(71) Applicant: S&W Seed Company, Five Points, CA (US)

(72) Inventors: Clinton C. Shock, Ontario, OR (US); Cheryl A. Parris, Ontario, OR (US)

(73) Assignee: S&W Seed Company, Hanford, CA (US)

( * ) Notice: Subject to any disclaimer, the term of this patent is extended or adjusted under 35 U.S.C. 154(b) by 142 days.

(21) Appl. No.: 14/544,200

(22) Filed: Dec. 8, 2014

(65) Prior Publication Data

US 2016/0165780 P1 Jun. 9, 2016

(51) Int. Cl.
*A01H 5/12* (2006.01)

(52) U.S. Cl.
USPC ..... Plt./258

(58) Field of Classification Search
USPC ..... Plt./263.1, 258
See application file for complete search history.

(56) References Cited

U.S. PATENT DOCUMENTS

| | | | |
|---|---|---|---|
| PP10,562 | P | 8/1998 | Sys et al. |
| PP10,563 | P | 8/1998 | Brandle et al. |
| PP10,564 | P | 8/1998 | Marsolais et al. |
| 6,031,157 | A | 2/2000 | Morita et al. |
| 6,080,561 | A | 6/2000 | Morita et al. |
| 6,255,557 | B1 | 7/2001 | Brandle |
| 7,862,845 | B2 | 1/2011 | Magomet et al. |
| 7,884,265 | B2 | 2/2011 | Morita et al. |
| PP22,593 | P3 | 3/2012 | Garnighian |
| PP23,164 | P3 | 11/2012 | Ramon Alvarez Britos |
| PP23,728 | P3 | 7/2013 | Ramon Alvarez Britos |
| 2009/0214753 | A1 | 8/2009 | Morita et al. |
| 2011/0023192 | A1 | 1/2011 | Morita et al. |
| 2011/0195169 | A1 | 8/2011 | Markosyan et al. |
| 2011/0271413 | P1 | 11/2011 | Garnighian |
| 2012/0058247 | A1 | 3/2012 | Shi |
| 2012/0090062 | P1 | 4/2012 | Alvarez |
| 2013/0347140 | A1 | 12/2013 | Wang |

OTHER PUBLICATIONS

Ali et al., Biochemical Investigation During Different Stages of in Vitro Propagation of *Stevia rebaudiana*, Pak. J. Bot., 42(4): 2827-2837 (2010).
Henderson, Jr. and Berry, Isocratic *Stevia* Sweetener Analysis using Selective Zorbax Columns: Application Note—Food, www.agilent.com/chem, Agilent Technologies, Inc. 5990-3933EN (Apr. 30, 2009).
Ahmed et al., An Efficient Method for in vitro Clonal Propagation of a Newly Introduced Sweetener Plant (*Stevia rebaudiana* Bertoni.) in Bangladesh, American-Eurasian Journal of Scientific Research 2(2):121-125 (2007).
Akita et al., Mass propagation of shoots of *Stevia Rebaudiana* using large scale bioreactor, Plant Cell Reports 13:180-183 (1994).
Anbazhagan et al., In vitro production of *Stevia rebaudiana* Bertoni, Emir. J. Food Agric. 22(3):216-222 (2010).
Midmore and Rank, A new rural industry—*Stevia*—to replace imported chemical sweeteners, Rural Industries Research and Development Corporation, Publication No. W02/022 (Aug. 2002).
Brandle et al., *Stevia rebaudiana*: Its agricultural, biological, and chemical properties, Can. J. Plant Sci. 78:527-536 (1998).
Brandle and Telmer et al., Steviol glycoside biosynthesis, Phytochemistry 68:1855-1863 (2007).
Dacome et al., Sweet diterpenic glycosides balance of a new cultivar of *Stevia rebaudiana* (Bert.) Bertoni: Isolation and quantitative distribution by chromatographic, spectroscopic, and electrophoretic methods, Process Biochemistry 40:3587-3594 (2005).
Debnath, Clonal propagation and antimicrobial activity of an endemic medicinal plant *Stevia rebaudiana*, Journal of Medicinal Plants Research 2(2):045-051 (2008).
Goettemoeller and Ching, Seed Germination in *Stevia Rebaudiana*, J. Janick (ed), ASHS Press (1999).
Jena et al., Effect of phytoregulators on in vitro mass propagation of *Stevia rebaudiana* Bertoni, International Journal of Integrative Biology, 8(1):56-59 (2009).
Kolb et al., Analysis of Sweet Diterpene Glycosides from *Stevia rebaudiana*: Improved HPLC Method, J. Agric. Food Chem. 49:4538-4541 (2001).
Madan et al., *Stevia rebaudiana* Bertoni—A Review, Indian Journal of Natural Products and Resources 1(3):267-286 (2010).
Reick et al., Improved HPLC method for the evaluation of the major steviol glycosides in leaves of *Stevia rebaudiana*, Eur. Food Res. Technology 231:581-588 (2010).
Sharma et al., Chemistry and in vivo profile of ent-kaurene glycosides of *Stevia rebaudiana* Bertoni—An overview, Natural Product Radiance 8(2):181-189 (2009).
Shatnawi et al., Clonal propagation and cryogenic storage of the medicinal plant *Stevia rebaudiana*, Spanish Journal of Agricultural Research 9(1):213-220 (2011).
Shimadzu, Analysis of Steviol Glycosides in *Stevia* Extract, Shimadzu Corporation Application News, No. L439 (2012).
Shock, Experimental Cultivation of Rebaudi's *Stevia* in California, University of California Davis, Agronomy Progress Report No. 122 (Apr. 1982).
Shock, Rebaudi's *stevia*: natural noncaloric sweeteners, California Agriculture 36(9) and (10), University of California Davis, Division of Agricultural Sciences Reports of Progress in Research (Sep.-Oct. 1982).
Tavarini and Agnelini, *Stevia rebaudiana* Bertoni as a source of bioactive compounds: the effect of harvest time, experimental site and crop age on steviol glycoside content and antioxidant properties, J. Sci. Food. Agric. 93:2121-2129 (2013).
Taware et al., Comparative studies of in vitro and in vivo grown plants and callus of *Stevia rebaudiana* (Bertoni), International Journal of Integrative Biology 9(1):10-15 (2010).
Yadav et al., A review on the improvement of *stevia* [*Stevia rebaudiana* (Bertoni)], Can. J. Plant Sci. 91:1-27 (2011).
International Search Report and Written Opinion for commonly owned PCT/US2015/060925 dated Jan. 29, 2016.
International Search Report and Written Opinion for commonly owned PCT/US2015/061185 dated Feb. 1, 2016.
S&W Press Release for SW 107 Varietal dated Dec. 1, 2014 (The SW 107 Varietal was filed as Plant U.S. Appl. No. 14/544,136, filed Nov. 30, 2014).

*Primary Examiner* — Keith Robinson

(74) *Attorney, Agent, or Firm* — Karen Canaan; CanaanLaw, P.C.

(57) ABSTRACT

A new and distinct *Stevia rebaudiana* plant named 'SW 201' is described. The new variety is distinguished from other *Stevia* varieties by excellent sweet leaf taste with very low bitterness and aftertaste, superior overwintering capability, high plant vigor, high leaf yield, late flowering, and high steviol glycoside levels.

4 Drawing Sheets

Genus and species: *Stevia rebaudiana*.
Variety denomination: 'SW 201'.

BACKGROUND OF THE INVENTION

*Stevia rebaudiana* is a plant species in the sunflower (Asteraceae) family, which has naturally sweet leaves. The active compounds that impart the sweet flavor to *stevia* leaves are steviol glycosides. The most common steviol glycosides are stevioside and rebaudioside A, both of which have up to 250 to 400 times the sweetness of sugar. Stevioside tends to be more prevalent in unimproved lines of *stevia* leaves than rebaudioside A. The development of new varieties of *Stevia rebaudiana* with higher levels of rebaudioside A than stevioside is desirable for use as a sugar substitute.

The present invention relates to a new and distinct variety of *Stevia rebaudiana*, the 'SW 201' line, which has very sweet leaves with high levels of steviol glycosides and very low bitterness and aftertaste, excellent overwintering, high plant vigor, high leaf yield, and late flowering.

The 'SW 201' line was derived in 2012 from a single plant in a population of recurrently selected *Stevia rebaudiana*, the population of which was originally grown from seed in an outdoor field in Chowchilla, Calif., USA, under natural lighting. The parentage of the 'SW 201' line is not known and population from which the 'SW 201' line was derived has no patented parental lineage. The plant that produced the 'SW 201' line was selected from its population based upon the following characteristics, which were measured and/or observed between 2012 and 2014.

Leaf Taste:

The leaves of the 'SW 201' line were found to have an excellent sweet taste in comparison to a majority of the plant population from which the line was derived and very little bitterness and aftertaste in comparison to most *stevia* varieties.

Overwintering:

The 'SW 201' line was found to have superior overwintering in comparison to the majority of the plant population from which the line was derived, the latter of which died over the course of the winter.

Plant Vigor:

The 'SW 201' line was found to have greater growth with higher leaf yield and later flowering (an advantage for leaf production) in comparison to the majority of the plant population from which the line was derived.

Steviol Glycosides:

The leaves of the 'SW 201' line were found to have high levels of steviol glycosides (over 18%) with rebaudioside A accounting for over 60% of the total steviol glycoside content in the leaves (see, Table 1).

Upon initial selection, the 'SW 201' line was asexually reproduced from rooted cuttings in May 2012. Plant yield and leaf quality of the 'SW 201' line were confirmed in April through October 2014 through replicated yield trials in the following three locations: Yuma, Ariz.; Indio, Calif.; and Ontario Oreg. At each of the three locations, the performance of the 'SW 201' line grown from cuttings was compared to seedlings of the 'Candy' line (Genesis Seed Ltd., Ashalin, Isreal; unpatented) grown from bulk commercial seed ("the check variety"). Table 1 compares various characteristics of an average sampling of leaves of the 'SW 201' line with an average sampling of leaves of the check variety.

TABLE 1

| | SW 201 | Check Variety |
|---|---|---|
| Percentage of Rebaudioside A | 11.17% | 6.85% |
| Percentage of Stevioside | 5.29% | 6.42% |
| Percentage of total Steviol Glycosides | 18.04% | 14.71% |
| Ratio of Rebaudioside A: Stevioside | 2.19 | 1.11 |
| Percentage of Rebaudioside A to total Steviol Glycosides | 60.9% | 46.8% |

The data in the foregoing table shows that in comparison to the check variety, the 'SW 201' line contained more rebaudioside A (11.17% vs. 6.85%); less stevioside (5.29 vs. 6.42%); more total steviol glycosides (18.04% vs. 14.71%); a higher rebaudioside A to stevioside ratio (2.19 vs. 1.11); and a higher percentage of rebaudioside A to total steviol glycosides (60.9% vs. 46.8%). In addition to the foregoing, the 'SW 201' line also produced 22% more leaf yield than the check variety with the 'SW 201' line producing 4,129 lb of leaf per acre per year versus 3,386 lb of leaf per acre per year for the check variety. Leaf yield results were averaged over three locations with four replications at each location, and two harvest strategies (one or two cuttings per year). The higher yield of the 'SW 201' line was due in part to low stand loss from *Fusarium* and other root diseases that reduced plant stand of the check variety.

BRIEF SUMMARY OF THE INVENTION

The following characteristics of the new 'SW 201' line have been repeatedly observed and can be used to distinguish the 'SW 201' line as a new and distinct cultivar of a *Stevia* plant:

1. Excellent sweet flavor to the leaves with very little bitterness and aftertaste;
2. Excellent overwintering;
3. High plant vigor;
4. High plant yield;
5. Late flowering;
6. Rebaudioside A content of 11.17%;
7. Stevioside content of 5.29%;
8. Total Steviol Glycoside content of 18.04%;
9. 60.9% Rebaudioside A to total Glycoside Steviol; and
10. Over 4100 lb. of leaf per acre per year.

BRIEF DESCRIPTION OF THE DRAWINGS

The accompanying photographs show, as nearly true as is possible in color illustrations of this type, typical flower and foliage characteristics of the 'SW 201' line. The plants depicted in the accompanying photographs are approximately one year old.

DETAILED BOTANICAL DESCRIPTION

Following is a detailed botanical description of a new and distinct variety of a *Stevia* plant known as 'SW 201'. Plant observations were made on Oct. 14, 2014, on mature one year old plants grown in a field in Ontario, Oreg., USA in natural light. The 'SW 201' line has not been observed under all possible environmental conditions. Where characteristics, such as dimensions, sizes, colors, and other such characteristics are given, it is to be understood that such characteristics are approximations or averages and that such approximations are not intended to be limiting. It is also to be understood that the phenotype of the variety may be altered by changes with environment, such as season, temperature, light quality, light intensity, day length, cultural conditions, and the like. Color notations are based on *The Royal Horticultural Society Colour Chart*, The Royal Horticultural Society, London, 2007.

Botanical classification: *Stevia rebaudiana* cultivar 'SW 201'.

Parentage: Seeds (unpatented) of Clinton C. Shock and *stevia* plants (unpatented) grown from the seeds in Chowchilla, Calif.

Figure 1:
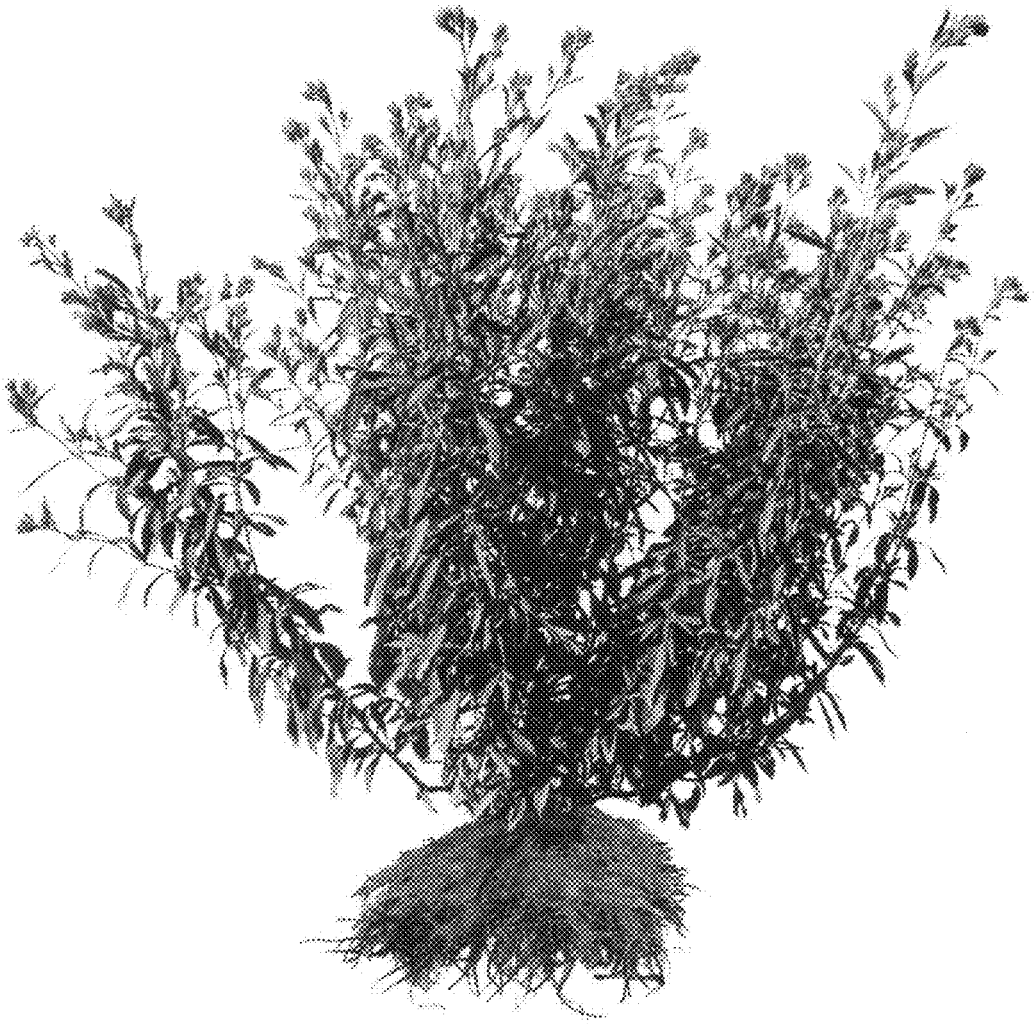
FIG. 1 depicts a color photograph of a fully mature 'SW 201' *Stevia* plant from roots to top of the plant near the end of the plant's first growing season.

Plant (description based on FIG. 1):

*Type*.—Perennial in climates with mild winter temperatures.
*Form and habit*.—Multiple branching bush.
*Height* (*from top of soil*).—90 cm.
*Width* (*including flowers*).—75 cm.
*Harvest cycle*.—Summer and fall or fall.

Figure 2:
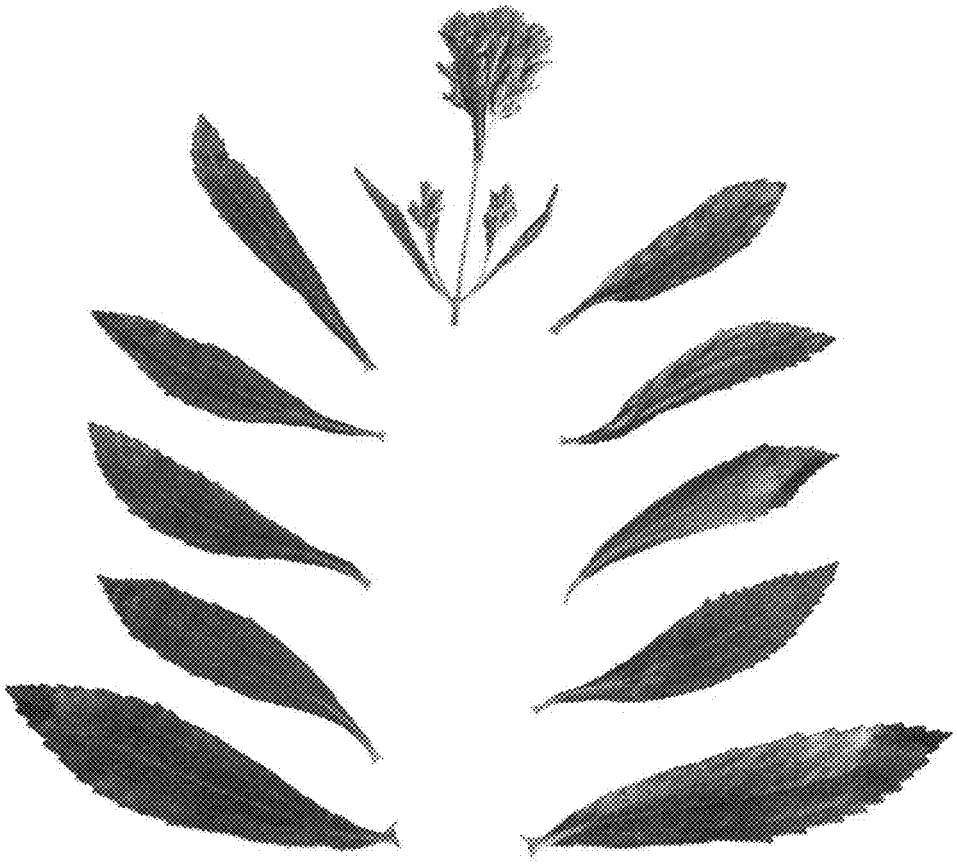
FIG. 2 depicts a color photograph of 'SW 201' leaves.
Figure 3:
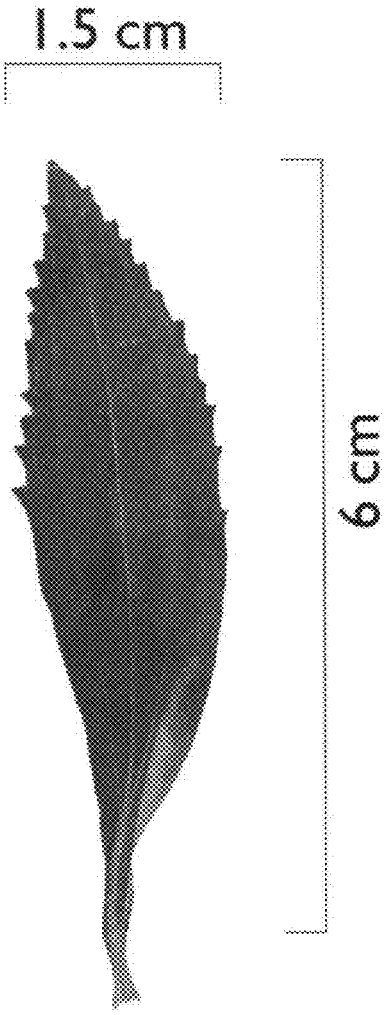
FIG. 3 depicts a color photograph of an 'SW 201' leaf, including the shape and dimensions.

Leaves (description based on FIGS. 2 and 3):

*Length*.—5.0 cm-10 cm.
*Width*.—1.0 cm-2.0 cm.
*Arrangement*.—Opposite.
*Shape*.—Lanceolate.
*Apex descriptor*.—Acute.
*Base descriptor*.—Cuneate.
*Margin descriptor*.—Serrate.
*Color, mature foliage*.—Upper surface. RHS137C. Lower surface. RHS137C.
*Color, veins*.—RHS 139C.
*Texture, mature foliage*.—Upper surface. Slight pubescence. Lower surface. Moderate pubescence.
*Petiole length*.—0.6 cm.
*Petiole diameter*.—0.3 cm.
*Petiole texture*.—Upper surface: Slight pubescence. Lower surface: Slight pubescence.
*Pubescence color*.—Upper surface. RHS 139C. Lower surface. RHS 139C.
*Stevioside content*.—5.29%.
*Rebaudioside A content*.—11.17%.
*Rebaudioside A as a percentage of total steviol glycosides*.—60.9%.
*Ratio of rebaudioside A to stevioside*.—2.19.
*Total steviol glycosides*.—18.04%.
*Leaf harvest period*.—Summer and/or Fall.

Stem:

*Length* (*excluding inflorescence*).—Varies to 1 m.
*Diameter*.—Varies to 2.0 cm.
*Texture*.—Pubescent.
*Color*.—RHS 145B.

Figure 4:
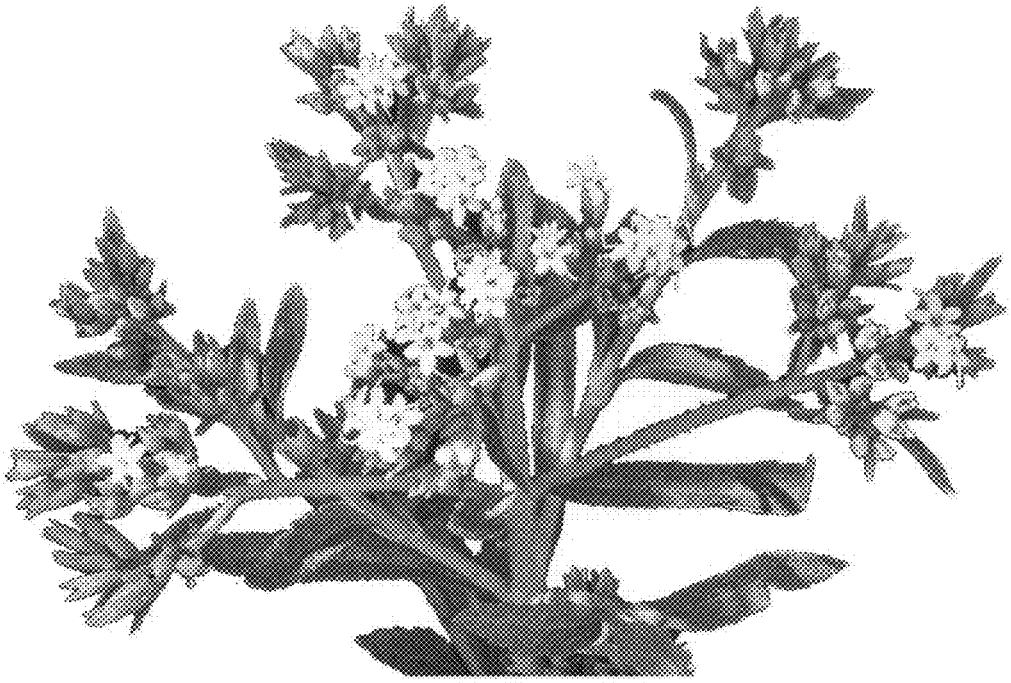
FIG. 4 depicts a color photograph of the flowers of an 'SW 201' *Stevia* plant.

Flowers (description based on FIG. 4):

*Inflorescence type*.—Panicle.
*Petal color*.—RHS N155D.
*Petal length*.—0.6 cm.
*Petal width*.—0.1 cm.
*Bloom period*.—October to November at Ontario, Oreg.
*Arrangement*.—Composite.
*Shape*.—Cluster.
*Fragrance*.—None.
*Number of flowers per capitulum*.—5.

Peduncle:

*Color*.—RHS 145B.
*Diameter*.—0.15 cm.
*Aspect*.—Perpendicular.
*Texture*.—Pubescent.

Pedicles:

*Color*.—RHS 145B.
*Diameter*.—0.03 cm.
*Aspect*.—45 degrees.
*Texture*.—Pubescent.

Disc florets:

*Arrangement*.—Radially symmetrical.
*Shape*.—Tubular.

Phyllaries:

*Quantity*.—5.
*Length*.—0.7 cm.
*Width*.—0.15 cm.
*Shape*.—Lanceolate.
*Apex*.—Acute.
*Base*.—Fused.
*Margin*.—Overlapping.
*Color*.—RHS 145B.

Reproductive organs:

*Androecium*.—Stamen quantity. 5. Stamen length. 3 mm. Stamen width. 0.5 mm. Anther length. 4 mm. Anther color. RHS 199A. Pollen amount. Medium pollen. Pollen color. RHS 4D.
*Gynoecium*.—Pistil length. 8 mm. Ovary length. 9 mm. Ovary width. Bipartite stigma of 4 mm. Ovary color. RD N999D. Style color. RHS N155B. Stigma color. RHS N155B.

Fruit and seed set:

*Flowering*.—October to November, which is later than most *stevia* line, which flower from mid-to-late September.
*Seeds*.—Small black (RHS 200C) achene with pappus attached typical of *Stevia rebaudiana*. Seed length. 3 mm. Seed diameter. 0.5 mm. Seed texture. Soft seed coat with ribbed texture.

Cold hardiness: Hardy to 23° F. (−5° C.) at Ontario, Oreg.

Heat tolerance: Hardy to a monthly average maximum temperature of 107-108° F. (42° C.) at Yuma, Ariz., and Indio, Calif.

We claim:

1. A new and distinct cultivar of *Stevia* plant named 'SW 201' as substantially shown and described herein.

* * * * *